US006449598B1

(12) United States Patent
Green et al.

(10) Patent No.: US 6,449,598 B1
(45) Date of Patent: Sep. 10, 2002

(54) HEALTH CARE POLICY ON-LINE MAINTENANCE DISSEMINATION AND COMPLIANCE TESTING SYSTEM

(75) Inventors: Gordon M. Green; Robin Anne Maley; Michael H. Barnett; Richard Eckerstrom; Richard Allen Kamm; Robert J. Keenoy; Donald Louis Mikkelsen, all of New York City, NY (US); Coleman L. Munch, Lafayette, CA (US); Jesse N. Randall; Michael Sanita, both of New York City, NY (US); Susan Ann Yubas, Purchase, NY (US)

(73) Assignee: Xware Compliance, Inc., New York, NY (US)

( * ) Notice: Subject to any disclaimer, the term of this patent is extended or adjusted under 35 U.S.C. 154(b) by 0 days.

(21) Appl. No.: 09/388,619

(22) Filed: Sep. 2, 1999

(51) Int. Cl.[7] .................. G06F 17/10; G06F 17/30; H04K 1/00; H04L 9/00
(52) U.S. Cl. .................. 705/2; 705/51; 707/5; 707/9; 707/10; 434/322; 434/323
(58) Field of Search .................. 707/5, 9, 10; 434/322, 434/323; 705/2, 51

(56) References Cited

U.S. PATENT DOCUMENTS

| 5,144,557 A | | 9/1992 | Wang et al. |
|---|---|---|---|
| 5,247,661 A | | 9/1993 | Hager et al. |
| 5,276,869 A | | 1/1994 | Forrest et al. |
| 5,377,355 A | | 12/1994 | Hager et al. |
| 5,758,358 A | | 5/1998 | Ebbo |
| 5,781,915 A | | 7/1998 | Kohno et al. |
| 5,802,518 A | | 9/1998 | Karaev et al. |
| 5,813,009 A | * | 9/1998 | Johnson et al. ............. 707/100 |
| 5,819,300 A | | 10/1998 | Kohno et al. |
| 5,826,237 A | | 10/1998 | Macrae et al. |
| 5,842,216 A | | 11/1998 | Anderson et al. |
| 5,845,067 A | | 12/1998 | Porter et al. |
| 5,850,219 A | | 12/1998 | Kumomura |
| 5,864,871 A | | 1/1999 | Kitain et al. |
| 5,867,821 A | | 2/1999 | Ballantyne et al. |
| 5,879,165 A | * | 3/1999 | Brunkow et al. ............ 434/322 |
| 5,890,129 A | | 3/1999 | Spurgeon |
| 5,890,176 A | | 3/1999 | Kish et al. |
| 6,112,049 A | * | 8/2000 | Sonnenfeld .................. 434/350 |
| 6,288,753 B1 | * | 9/2001 | DeNicola et al. ............ 348/586 |
| 6,289,450 B1 | * | 9/2001 | Pensak ........................ 713/167 |

FOREIGN PATENT DOCUMENTS

EP    1 139 260 A1  * 10/2001

OTHER PUBLICATIONS

Quality Research for Quality Health Care—Centers for Education and Research on Therapeutics—www.ahcpr.gov/about/qr4qhc/qr4ahc–3.htm, printed Apr. 18, 2002, pp. 1–7.*

* cited by examiner

Primary Examiner—Robert P. Olszewski
Assistant Examiner—J Harle
(74) Attorney, Agent, or Firm—Robert L. Epstein; Harold James; James & Franklin, LLP

(57) ABSTRACT

The software based interactive system provides accessibility to an institution's own policies via either an internet web site or an intranet home page. Qualified users may search for and access documents related to institution policies for review, including a list of those which the user is required to know. Where required, a test is provided to the user. The responses are scored and the results stored. Administrative users can set and change qualification parameters as to individual, group and/or institution-wide policy access and receive individual, group and/or institution-wide test results. Identification of incomplete, contradictory or obsolete policies, policies awaiting approval, policies due for review and data on user review of policies can be reported.

20 Claims, 14 Drawing Sheets

HEALTH CARE POLICY ON-LINE MAINTENANCE DISSEMINATION AND COMPLIANCE TESTING SYSTEM

The present invention relates to health care policy compliance and more particularly to an on-line software based system which stores health care policy documents for searching and access by qualified users, provides user self-tests, records and reports the test results to the user and to administration to insure compliance.

Personnel employed by health care related facilities, such as hospitals, home health care agencies, nursing homes, pharmacies, health maintenance organizations and the like, must follow an ever increasing number of detailed procedures, guidelines, rules, laws and/or regulations imposed by external agencies (government, regulatory and accrediting bodies) which are required for various medical and/or legal considerations. Policies are developed within institutions to guide their personnel in complying with these requirements. Because different personnel with different responsibilities in different departments are required to be familiar with multiple policies, large institutions are encountering increasing difficulty insuring that each individual is reviewing and comprehending the specific policies he must comply with.

For example, physicians in an emergency room are required by Federal law and regulations (the Emergency Medical Treatment and Active Labor Act) to follow specific procedures for treating and/or transferring patients to other healthcare facilities. Nurses, on the other hand, may need to know policies regarding isolation procedures for patients with infectious diseases. Everyone at the hospital may have to know about requirements of the hospital's disaster plan or regulations concerning nondiscrimination and OSHA requirements.

It is difficult for the hospital to know if all personnel have reviewed and adequately understand the policies appropriate for their particular responsibilities, department, rank, etc. Further, certain governmental agencies require that health care facilities report compliance by their personnel by verifying that their personnel have in fact reviewed and demonstrate an understanding of the necessary policies.

The present invention is an on-line, software based system designed to assist health care institutions to manage the burden of maintaining and disseminating policy information to the appropriate individuals employed in various capacities throughout the organization. The system functions as a centralized reference, making policy materials available to all personnel in an easily searchable and quickly accessible form. The system also restricts access to particular materials to qualified users and keeps track of which individuals have reviewed which policies and when. It can verify each user's comprehension with self-administered tests. The test results can be summarized and reviewed by administrative personnel to determine and, if need be, report compliance statistics for individuals, groups or institution-wide or structure remedial training/education programs.

The present invention benefits an institution by increasing the quality of the policies themselves, increasing the staff's level of understanding and familiarity with policies (and therefore, compliance with them), providing an integrated methodology for creating, approving, disseminating and maintaining policies, reducing litigation risks and expenses and reducing policy management and compliance costs in terms of both dollars and manpower resources. Forms utilized by the institution (consent, test requests, purchase orders, etc.) are also maintained on the system, eliminating the costs of printing, inventorying and distributing the forms throughout the institution. The institution is always assured that the most current version of these forms will be accessed by the staff.

In general, these objectives are achieved by the system of the invention by maintaining a central database containing policies and related documents accessible on the World Wide Web or via an intranet home page by staff members who identify themselves with an appropriate log-in identification code. The documents in the database are searchable by a variety of customized parameters, enabling quick and easy access to documents on particular topics.

The document management functions of the system make users' access to policies much faster and easier than looking up policies in hard copy policy manuals. A user can quickly access the set of policies for which he is responsible, or the set of policies which meet the user's search criteria. In addition, links and searching capabilities simplify getting access to all policies relevant to an issue. This helps to quickly focus the user's attention on relevant information. The glossary and FAQs (Frequently Asked Questions) features provide users with additional interpretation/clarification of policy language.

Users see only the current versions of policies. Policies which are no longer current are archived, and are accessible only by a separate, restricted archival search function.

Selected users can access policies from off-site locations, an especially important function for the on-call physicians and administrator. In the event of a disaster, for example, the hospital or emergency room receives victims of a train crash, an Administrator or physician could access a hospital's emergency plan from his home or other remote location and immediately initiate appropriate response teams to treat the injured.

New or updated policies can be distributed by managers and accessed by users immediately. The costs and mistakes associated with distribution of hard copies and collection and/or destruction of obsolete policies are eliminated.

Current versions of forms are made readily available. The use of obsolete forms and the cost of maintaining a forms inventory are eliminated.

Management of the policies themselves is improved. The creation and revision of policies is streamlined. The authoring procedure helps administration establish and maintain institution wide standards for the technology and methodology used to create, maintain and organize policies. This improves consistency among policies, and assists the institution in adhering to policy content standards. Further, integration of policies with regulatory/accreditation standards is improved by the linking capability of the system.

Use of a search methodology incorporating expert knowledge and historical data improves the identification and handling of duplicate, overlapping or contradictory policies.

Automated management of the policy approval process organizes and accelerates the approval of policies. An individual whose approval is required on a policy before it is published is automatically notified, so that policy can be accessed for review. The system provides each approver with a list of policies awaiting approval, and it provides administrators with information on each policy's approval status (i.e., which approvals have been obtained and which are still pending).

Automated archiving of outdated policies creates a historical record of policies in effect at any given time. In the event of litigation in which policy compliance is an issue, archived documents can be easily accessed for response to discovery requests. The ease and efficiency of the retrieval process provides substantial cost savings.

Policy compliance is improved by the system. The system is designed to increase the level of staff awareness and comprehension of an institution's policies in several ways. A special feature enables each user to focus specifically on the policies for which he is responsible. Searching is set up to make it easy for a user to locate needed policy information, making it more likely that a user will actually refer to a policy for guidance.

Testing helps to increase policy familiarity and comprehension. A user can test his own understanding of particular policies, and test results can be stored for analysis. Results can be reported on an individual user basis to identify which policies a particular user understands and which policies required additional study. Results also can be reported on a policy basis to evaluate policies for clarity and understandability (consistently low scores by many users may indicate that a policy is not clear) and to identify policies for which additional training may be needed. The increase in the level of staff awareness and comprehension of the institution's policies reduces exposure to fines and/or lawsuits resulting from employee policy non-compliance.

Institution administrators can track who has reviewed a document, who has taken a test on the contents of the policy and the test results. Reports can be generated to demonstrate who has viewed and/or tested the policies by location, department, date, range, employee status and other parameters which are customizable as required.

Upon entering the web site, a main page is displayed. The main page is customizable by the institution. For example, if certain news is to be disseminated, the designated site administrator can simply input the information into the system for display on the main page, which each user will see as the user enters the system.

The system utilizes standard web technologies to deliver policy information to qualified users. Microsoft Windows NT is one operating system which can be used for the HTTP and application server. However, other operating systems could be used. The system is designed to support a wide range of web browsers. Other web browser enhancements may also be incorporated into the system for extra features.

Database tables keep information on when a document was created, by whom it was created, when it was last modified and by whom, for auditing purposes. The system keeps track of all users who logged on to the system, the policies they have reviewed and when same were reviewed. The system can also report on the number of hits and the number of reviews per document.

For security purposes, access to documents may be limited or based on personnel status. Codes or "tags" are inserted into the document to identify attributes and for formatting purposes.

It is, therefore, a prime object of the present invention to provide an on-line, software based, health care policy document maintenance, dissemination and compliance system.

It is another object of the present invention to provide such a system wherein all of the policies for an institution can be stored in a central database, accessible on the World Wide Web or via an intranet home page, by qualified users.

It is still another object of the present invention to provide such a system wherein the database is easily searched and the documents are readily accessible.

It is still another object of the present invention to provide such a system which keeps track of who has accessed which policies to insure that review of same, which may be mandated by regulating agencies, has actually occurred.

It is still another object of the present invention to provide such a system which is capable of assessing comprehension by having personnel who review a policy take a self-administered test, where the test results are stored and reported to designated administrators.

In accordance with one aspect of the present invention, a computer system is provided which includes a database capable of storing health care policy documents for selected access by authorized users via the Internet or an intranet home page. It is also capable of testing the user and reporting of test results for user feedback and administrative compliance purposes. The system includes means for storing data representative of document characteristics, means for storing data representative of user attributes and means for storing criteria for matching user attributes with document characteristics. Means are provided for storing documents. Means are provided for identifying users qualified to access the database. Means are provided for selecting stored documents based on the stored document characteristics data. Means are provided for determining whether an identified user is qualified to access selected stored documents, based on said stored matching criteria, as are means for permitting the user access to the selected stored document, if qualified. Means are provided for providing a test for the qualified user, as are means for grading the test and for recording the test results.

The means for storing documents includes means for determining if a document includes the required attributes, means for determining if the document is a duplicate of a document already stored, means for checking to determine if a document complies with storage requirements, means for incorporating revisions into the documents, if required, and means for recording the document.

Means are provided for storing data indicating that a test is required for a selected document, as are means for storing the test.

The means for storing document characteristics data includes means for storing document categories, means for storing document attributes and means for storing document types. The stored document selecting means includes means for locating documents based on the stored document categories, the stored document attributes and the stored document types.

Means are provided for reporting the test results to the user. Means are also provided for identifying qualified administrative users and for reporting the test results to them. Also included are means for tabulating test results by category.

In accordance with another aspect of the present invention, a method is provided for storing health care policy documents at a central database for selected access by authorized users on the Internet or via an intranet home page, and for testing the user and reporting of test results for user feedback and administrative compliance purposes. The method includes the steps of storing data representative of document characteristics, storing data representative of user attributes, storing criteria for matching user attributes with document characteristics and storing the documents. Users qualified to access the database are identified. Stored documents are selected based on the stored document characteristics data. It is determined if an identified user is qualified to access selected stored documents, based on the stored matching criteria. The user is permitted access to the selected stored document, if qualified. A test is provided for the qualified user. The test is graded and the test results are recorded.

The step of storing the documents includes the steps of determining if a document includes the required attributes, determining if the document is a duplicate of a document already stored, checking to determine if a document complies with storage requirements, incorporating revisions into the document, if required, and recording the document in the database.

The method further includes the steps of storing data indicating that a test is required for a selected document and storing the test.

The step of storing document characteristics data includes the steps of storing document categories, storing document attributes and storing document types. The step of selecting stored documents includes the step of locating documents based on the stored document categories, the stored document attributes and the stored document types.

The method further includes the step of reporting the test results to the user.

The method further includes the step of identifying qualified administrative users and reporting the test results to the qualified administrative users.

The method further includes the step of tabulating test results by category.

To these and to such other objects which may hereinafter appear, the present invention relates to an on-line health care policy document, maintenance, dissemination and compliance testing system and method, as described in the following specification, set forth in the annexed claims, taken together with the accompanying drawings, wherein like numbers refer to like parts, and in which:

Figure 1:
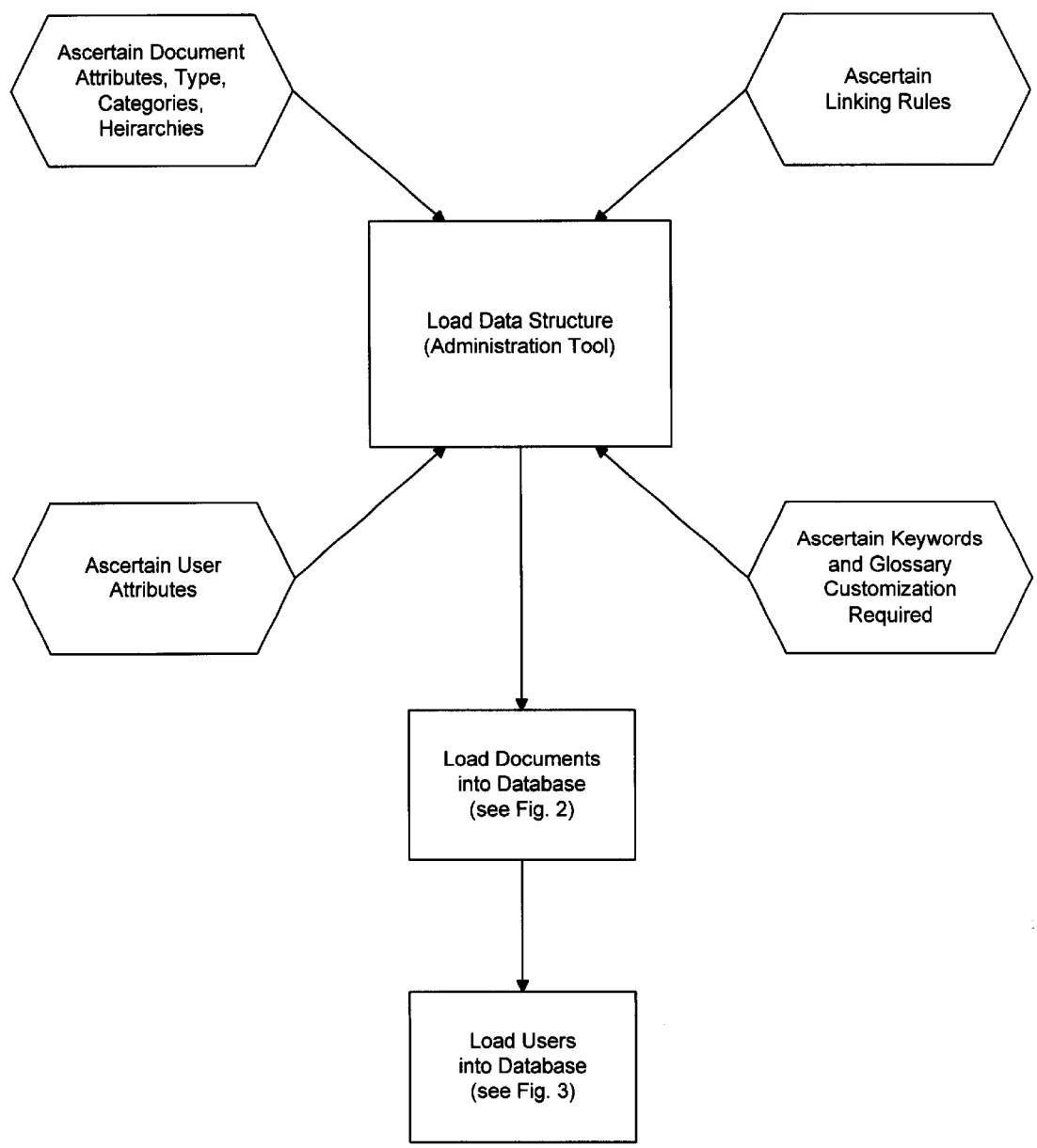
FIG. 1 is a flow chart depicting the setup of the system of the present invention.

As depicted in FIG. 1, the system of the present invention is set up by loading certain information obtained from the institution into the database. Characteristics of the institution's documents are identified. The system uses these characteristics to select, organize and display various subsets of the documents as required by the institution. A document characteristic may be an attribute, a document type or a category.

Using templates developed for the type of institution (hospital, HMO, etc.) as a starting point, the document categories are defined (e.g., admission policies, discharge policies, medical waste disposal policies, etc.), the document attributes (e.g., supersede date, effective date, last review date, section name and document type are defined, the document type values (e.g., policies, forms, job descriptions, etc.) are defined and a category hierarchy is created.

User attributes, which control distribution of the documents, are defined (e.g., level of responsibility, type of responsibilities, department, etc.). The rules for linking or matching documents with users are defined by specifying criteria based on document and user attributes. Each rule defines a relationship between a set of users and a set of documents (e.g., all nurses are required to know all medical waste-disposal policy documents). The relationships may be of various types. For example, a rule may say that documents with a "Department" attribute value equal to "Operating Room" must be reviewed by all users having a "Department" attribute equal to "Operating Room." This rule determines the parameters of the relationship between individual users and individual documents.

Based on information gathered from the institution, the glossary and keyword lists associated with the documents are customized by adding institution-specific terms.

All of this data is stored in the database. This data defines the institution's data structure. It makes it possible for the system to find, organize and display data quickly and easily.

Figure 2:
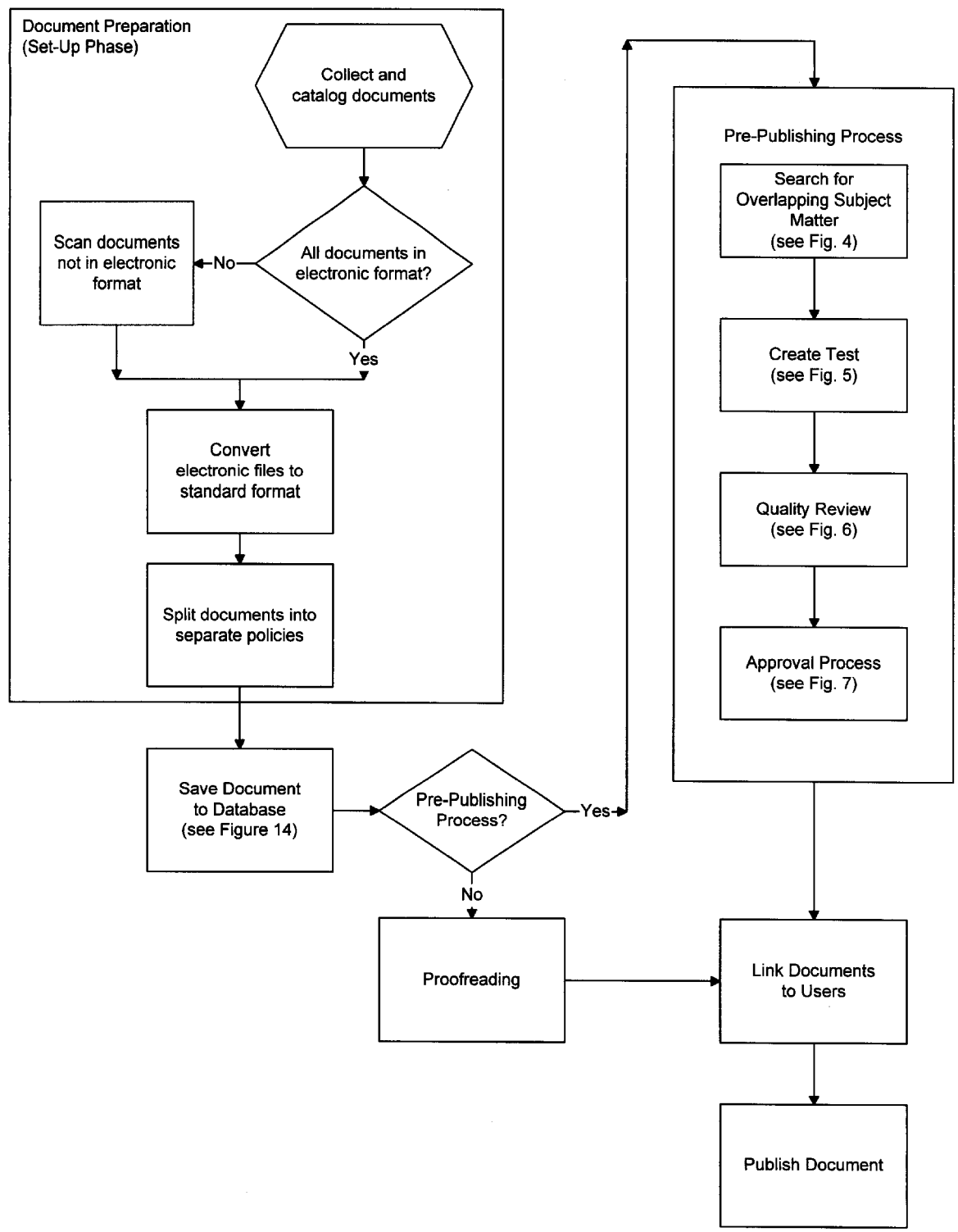
FIG. 2 is a flow chart depicting the document input process.

Documents are put into the data base by the process depicted in FIG. 2. This flow chart illustrates the steps involved in adding a document to the system and conforming the document to the standards of the institution. The steps generally include a setup phrase where documents are collected and formatted. The documents are then saved in memory and go through a prepublishing process, determining what changes in the document are required to meet the institution's standards for documents and insuring that the document has the necessary institutional approvals. Then, the document is published so it is available to qualified users.

During installation of the system, all documents are gathered together and prepared for input to the system. Experts work with hospital personnel to collect all hospital policies. Information regarding the hospital's system of organization for policies is gathered, and the policies are catalogued to insure that a clear record exists of what policies have been submitted for input into the system. As part of the cataloging process, it is determined which documents do not exist in electronic format. Documents which are not available in electronic format are scanned, and Optical Character Recognition software is used to create an electronic text file of the document. Document files which are not in standard format are converted. Electronic files may contain documents which actually comprise more than one policy. These must be separated and saved as separate files, so that each file consists of a single policy.

Figure 14:
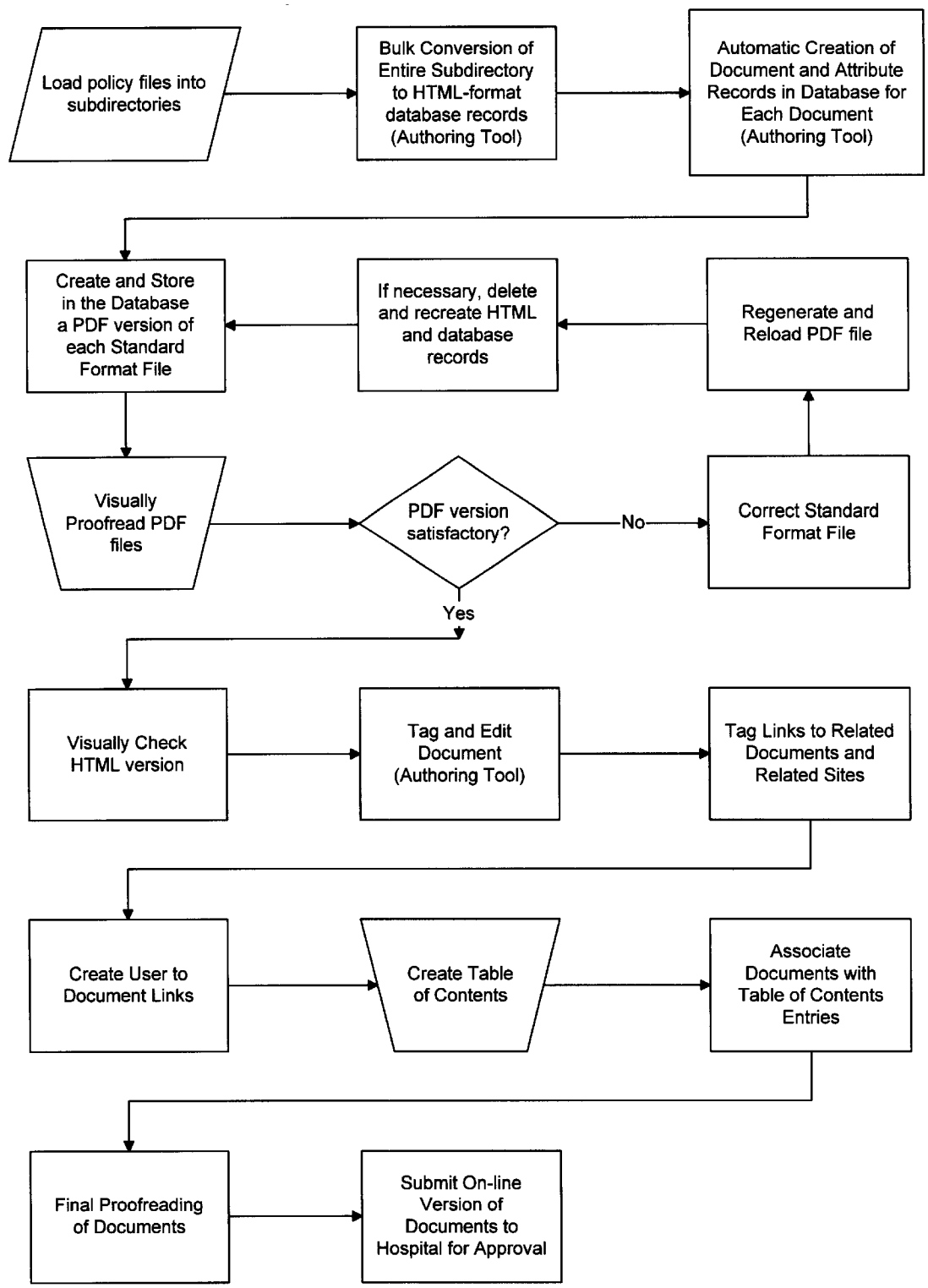
FIG. 14 is a flow chart illustrating the steps in storing a document in the database.

The document is saved by inserting it into the database by the process illustrated in FIG. 14. A determination is made as to whether the document is to be subjected to the pre-publishing process. Under some circumstances (initial setup or in an emergency situation in which a policy must be disseminated to users very quickly) administrators may decide to bypass the pre-publishing process and publish the document immediately. This is done by setting the document's status to "Published".

Figure 4:
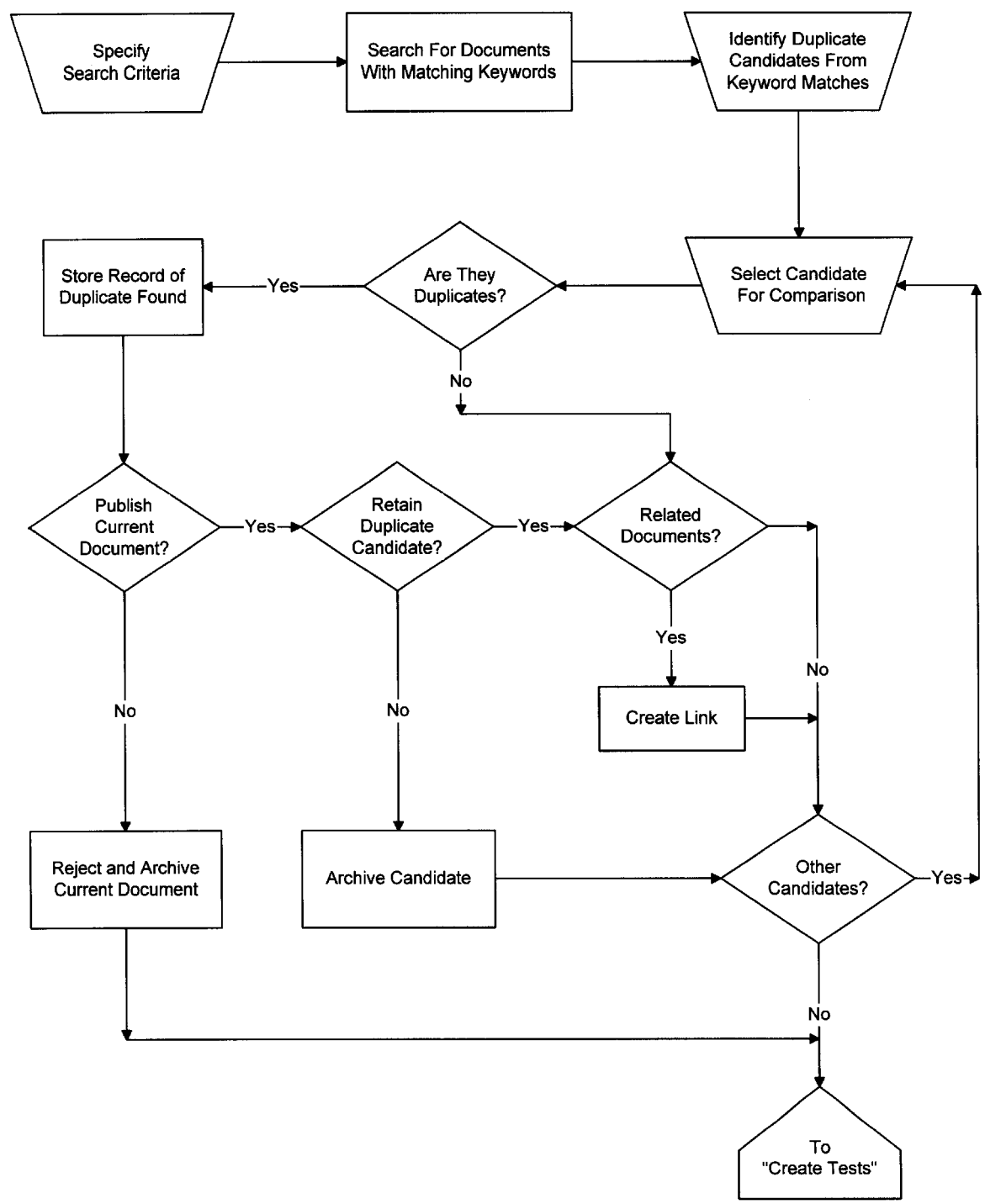
FIG. 4 is a flow chart depicting the steps involved in searching documents for overlapping subject matter.

The pre-publishing process includes a search of the database for duplicate, overlapping and contradictory policies. This is illustrated in FIG. 4.

Figure 5:
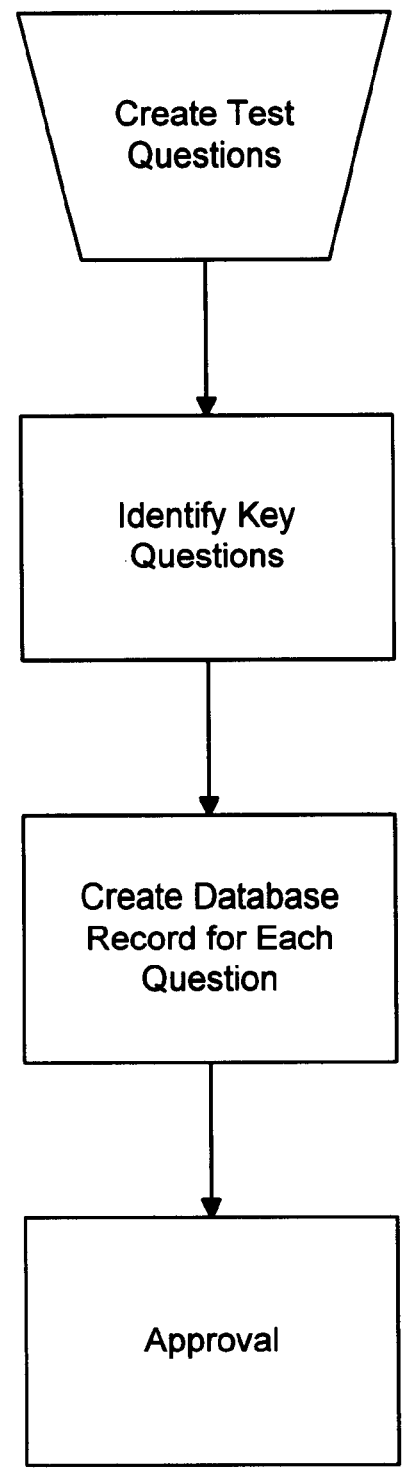
FIG. 5 is a flow chart depicting the steps in test creation.

If administrators determine that a test is required, the test is created. FIG. 5 illustrates the test creation process in greater detail.

Figure 6:
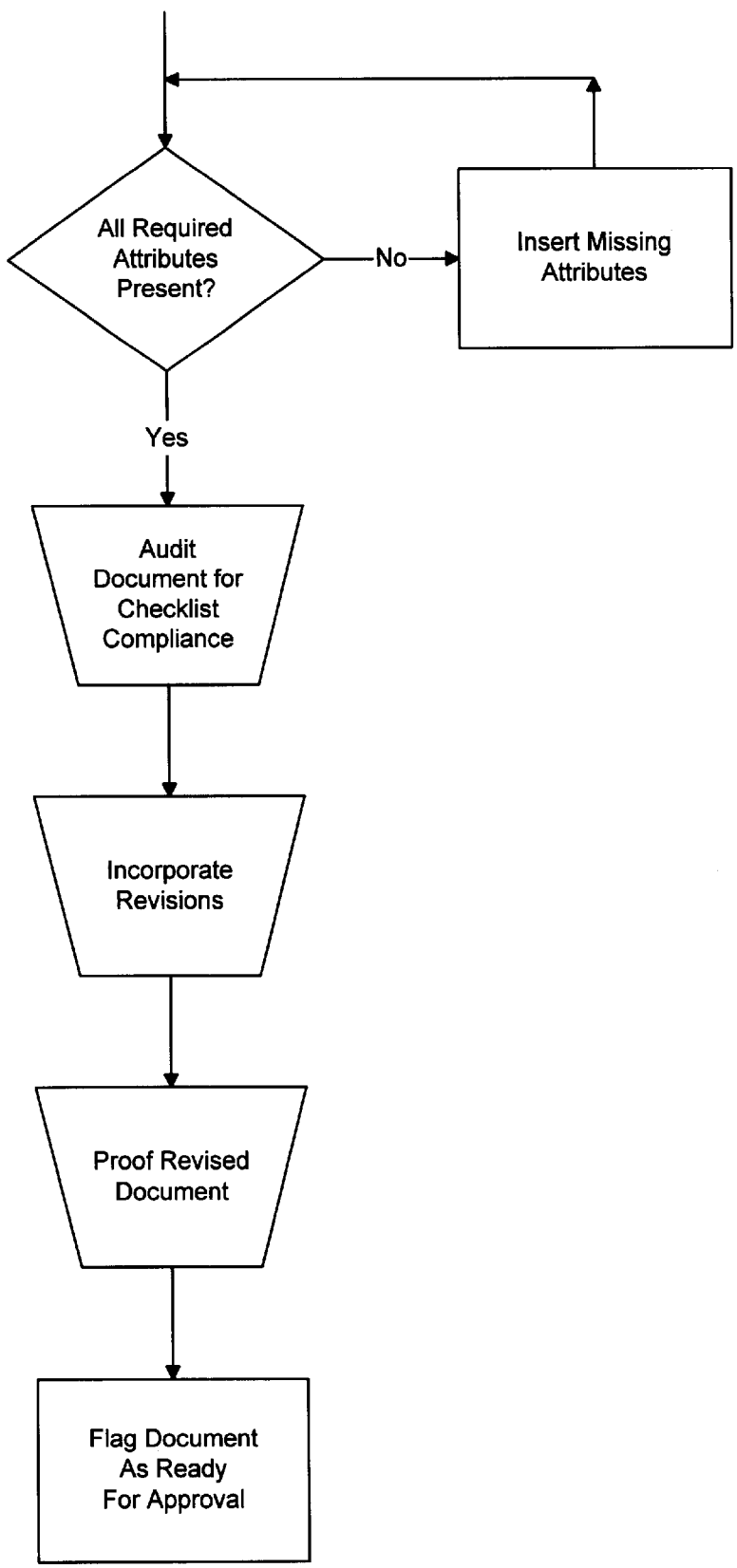
FIG. 6 is a flow chart of the quality review process.

Then the document is reviewed to determine whether it meets the standards set by the institution. This quality review process is illustrated in FIG. 6.

Figure 7:
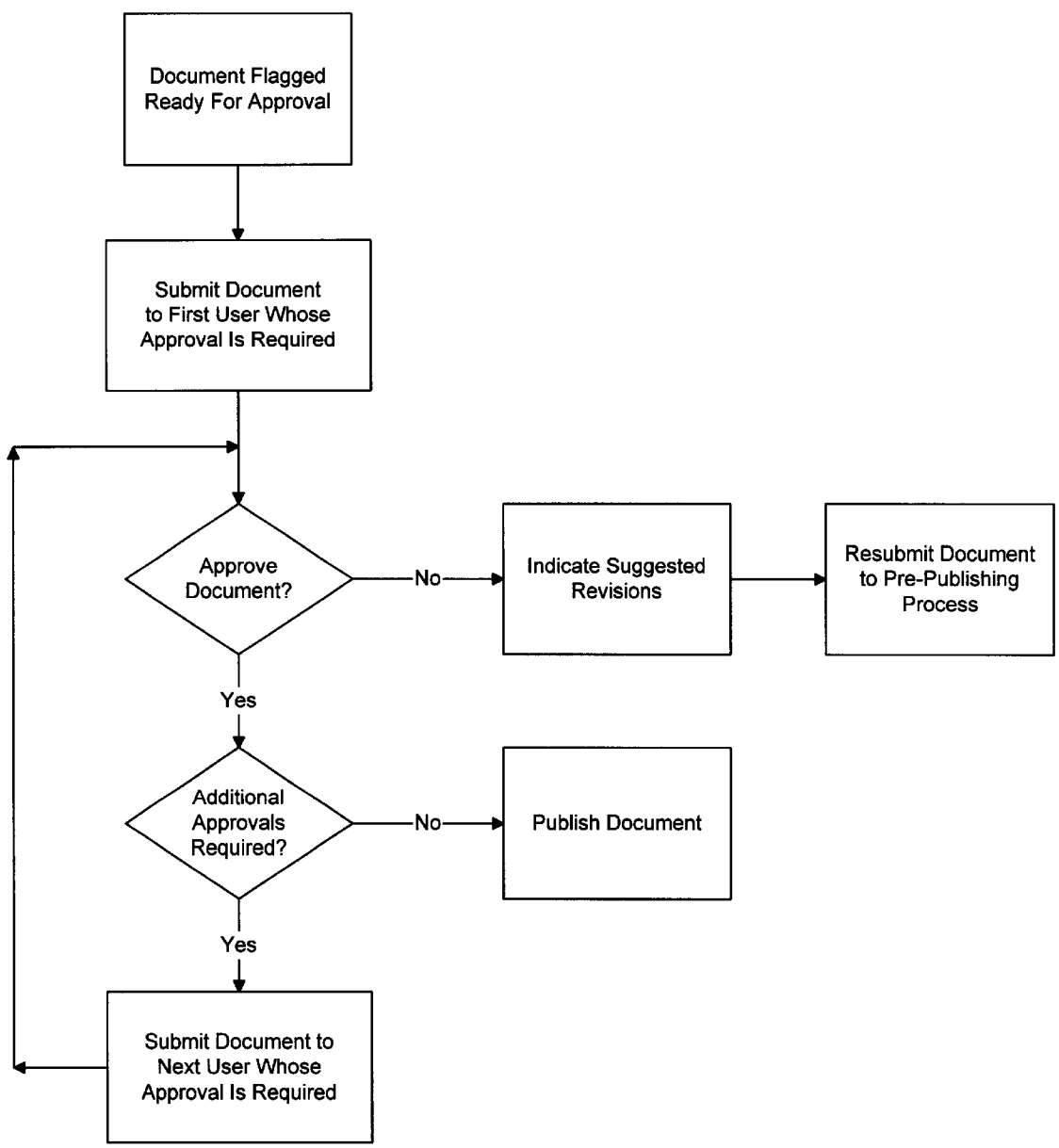
FIG. 7 is a flow chart of the steps in the document approval process.

All required approvals of documents are obtained. This approval process is illustrated in FIG. 7.

Figure 8:
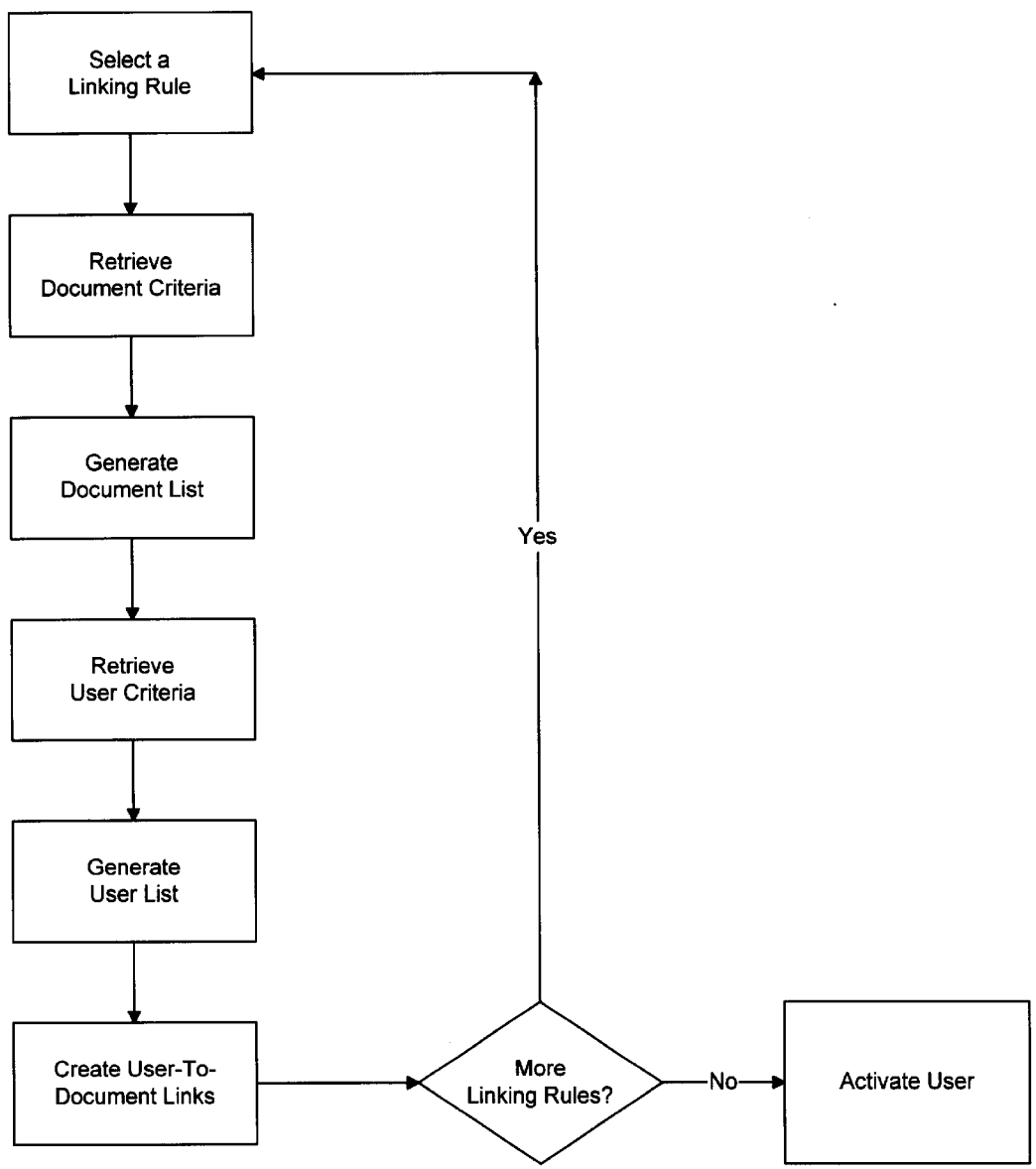
FIG. 8 is a flow chart of the process for creating user to document links.

As a final step before the document is published, the linking process, illustrated in FIG. 8, is performed to create links between the document and all of the users who are responsible for complying with the policy set forth in the document.

Once successfully through the pre-publishing process, the "Published" attribute of the document is set to "Yes" and the document becomes available to qualified users for searches and display. The document can be located through the "search" and "browse" functions and is automatically included in the list of required policies for the appropriate users. In this way, the system makes users immediately aware of new polices or revised policies for which they are responsible.

If the document is determined not to be put through pre-publication, it is simply proofread before it is introduced into the process by which user to document links are created.

Figure 3:
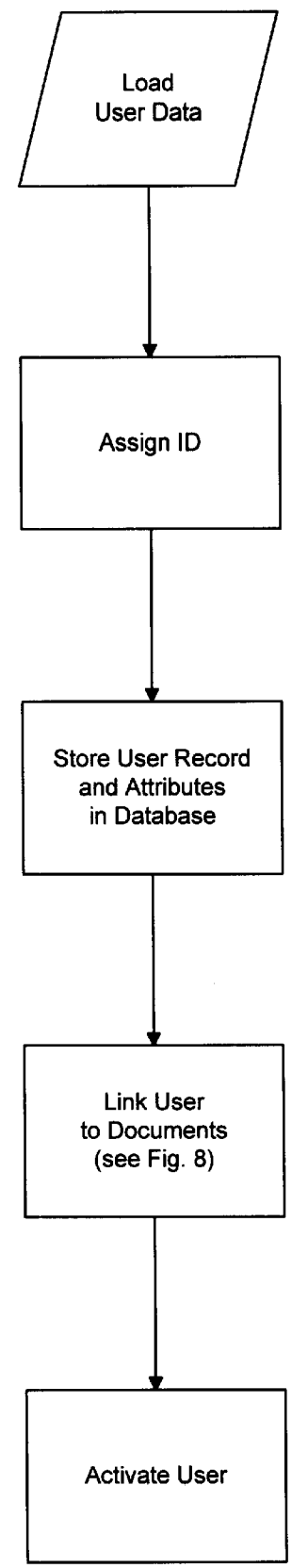
FIG. 3 is a flow chart depicting the user input process.

FIG. 3 illustrates the introduction into the system of information relating to the individual users. User data may be provided by the institution as a bulk file for the initial setup of the system, as a regular feed from other systems within the institution which maintain employee records, or manually, through an input interface. When received, it is loaded into the system storage. A unique ID is assigned to each record and a user record is stored in the database. Also, each user's attributes are stored as records in the database.

By the process illustrated in FIG. 8, links are created between the user and all documents which that user is responsible for complying with. The user is "activated" by setting a flag indicating that the user can log in and use the system.

As illustrated in FIG. 4, manual and automated searches are conducted to determine whether the document is redundant (already in the system) or contradictory (as compared to already stored documents) or obsolete. If any of these problems are indicated, the document is flagged for a decision whether to modify it before it can progress further in the parsing process. Automated searches are based on experience-based assumptions about probable sources of duplication.

The search begins by choosing criteria to narrow the search for documents which are duplicates of the current document or which include redundant or contradictory information. Criteria are chosen based on expert knowledge and historical data gathered from previous searches.

Focused by the specified search criteria, a search is done for documents with matching keywords. From the list obtained by the keyword search, an expert selects possible candidates for side by side comparison with the current document. One of the possible candidates is then selected for comparison.

A comparison between the selected candidate and the current document is made. If the documents are duplicates, a record of the duplicate match is stored. As these duplicate match records accumulate, they provide data to improve the specification of search criteria for future searches.

A decision is made whether the current document should be published or whether it should be rejected as a duplicate of a previously stored document and archived. If it is decided to retain the current document, a decision is made whether to also retain the previously stored duplicate document. If it is decided not to retain the previously stored document, it is archived, that is, transferred to a memory section not normally accessible to users.

If the previously stored document is to be retained, a decision is made whether the two documents should be linked as related documents. If so, a link is created and stored in the database. This process is repeated for each candidate document. Whether a test is required for the contents of the document is determined. If it is, a test is created, as illustrated in FIG. 5. This is often related to governmental regulations but may be based on the institution's internal quality control requirements.

The test is prepared by having a list of questions about the subject matter of the document created by experts. When a user requests a test, a selection of questions is randomly chosen from the question list for the document. Certain key questions may be identified which will always be included in the list of questions selected when a user requests a test.

A record is created for each question and stored in the database. The record includes the question itself, a reference to the document, a "key question" identifier and the correct answer to the question. The test is then submitted to the institution for approval.

Prior to approval of a document for publication, a quality review is conducted to audit the document for compliance with the check list. Any necessary revisions in the document may be made at this point and the document is either approved for publication or the institution is notified of the reasons for non-approval.

As seen in FIG. 6, quality review begins with a check to see whether values are stored in the database for all document attributes required by the institution's standard for this type of document. If required attributes are missing, they are added. An audit is conducted by experts against the document checklist to assess whether the document meets the institution standard for this type of document in other respects. Revisions are made, if required. The revised document is proofread and the document's status is set to "Ready for Approval".

The approval process is illustrated on FIG. 7. the system provides a means for storing with each document information regarding the approvals required to publish the document. If more than one approval is required, the information stored by the system includes information as to the order in which the required approvals must be obtained. The system then presents the document to each approver in turn. Once that person has indicated (on-line) his approval, the system records the approval and submits the document to the next person whose approval is required. If the approver does not approve of the document in its current form, he can indicate proposed revisions on line. The document with proposed revisions is then resubmitted to the Pre-Publishing Process. When all necessary approvals are indicated on the document, the document's status is set to "Publish". In this way, the system automatically moves the document through the sequence of approvers. At any time the approval information stored with the document provides administrators with the current approval status of the document.

FIG. 8 illustrates how "user to document" links are created. Each linking rule specifies a relationship between a set of documents and a set of users. The linking process identifies the set of documents and the set of users whose relationship each rule defines.

First a single linking rule is selected for processing. The linking rule specifies document attribute values which are used as parameters for a database query and retrieves same from the database. A list of documents having the specified attribute values is returned from the database in response to the query.

In a similar manner, user attribute values specified by the linking rule are used as parameters for a database query. A list of users having the specified attribute values is returned from the database in response to the query.

Links are created between each of the documents in the document list and each of the users in the user list. Each of the links created is stored in the database. A check is made to determine if any linking rules remain to be processed. If so, the next rule is selected and processed in the same manner. If no more rules remain to be processed, the user is activated.

Users access the system by logging on to the institution's home page, which provides access to the functions of the system. From there the user can access policy information in four ways: He can quickly access "Priority Policies" which have been selected for particularly quick access. He can search for policies based on criteria such as subject, date, or keywords. He can browse through all policies in a particular category, such as a department. He can also retrieve a list of the policies which he is responsible for knowing.

The time and effort required to look up policies in policy binders is eliminated. The number of policies which the user must look through is dramatically reduced. Through the "My Policies" function, which maintains a list of policies which each user is required to know, the system helps the user to focus on the policies for which he is actually responsible. In addition, the system provides links to related documents, a glossary, and a list of Frequently Asked Questions (FAQs) relating to each document to provide the user with additional information for clarification and explanation of the policies.

Thus, the system helps users to easily locate the information they need and to understand the information they find. Users' comprehension of policies is increased, and thereby compliance with the policies is increased as well.

Figure 9:
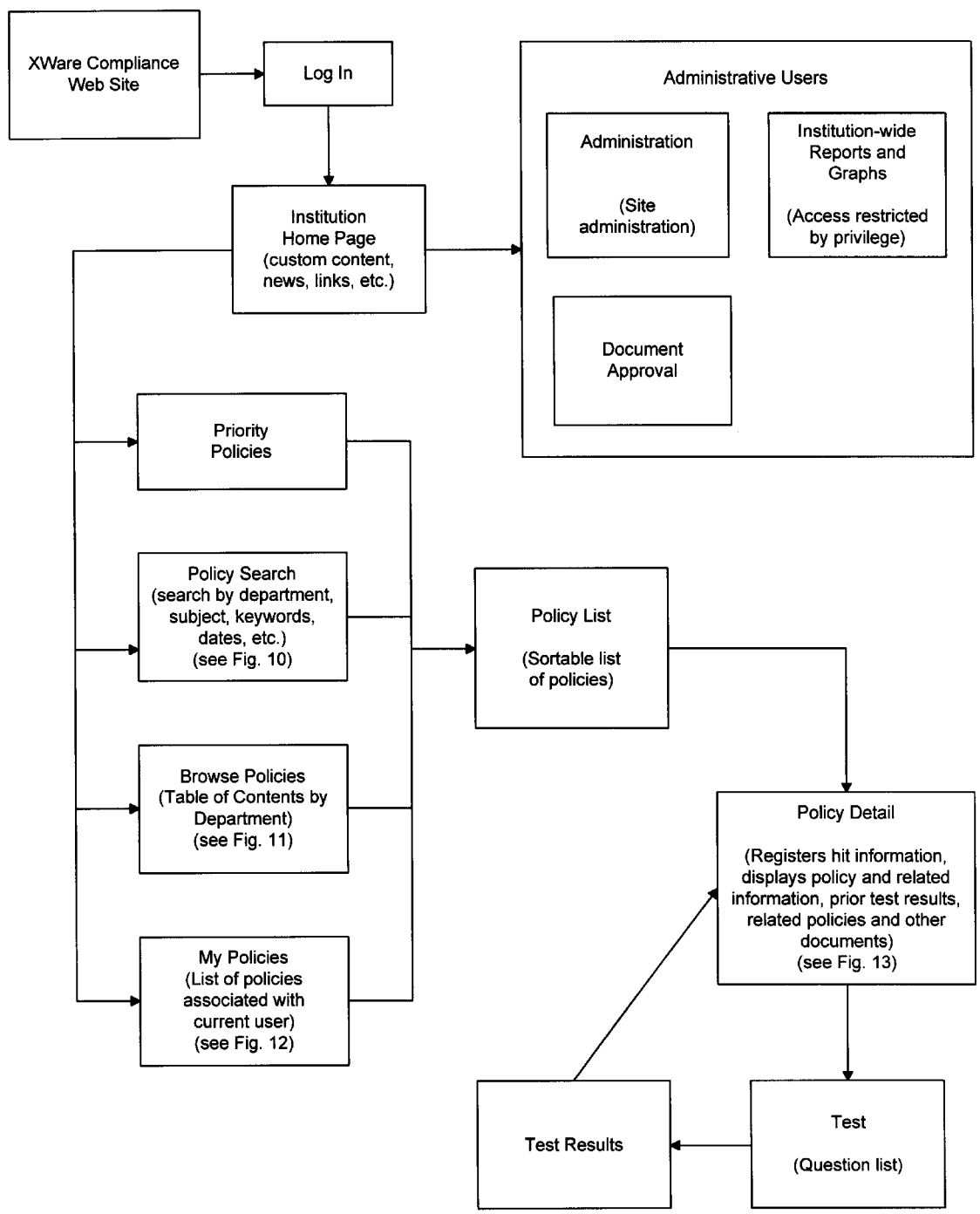
FIG. 9 is a flow chart illustrating the page flow through the system.

FIG. 9 is a page flow diagram showing how the system provides the user with documents for review and with test materials, when necessary. Further, it illustrates how compliance is reported to the institution administrators.

The entry point into the system is a web site, if an Internet configuration is selected. However, the system could be connected directly to the internal computer network of the institution, either on-site or via dedicated communication lines.

Each user must enter a User ID and a password to "log in" to the system. In addition to providing security for the database, the User ID/password is used by the system to control access to particular documents or sets of documents, as well as to restrict access to the administrative functions. Upon successful log in, the user is provided with a customized institutional home page. The home page can provide any current information, such as important news or announcements, as well as links to other web sites, if desired.

From the institution home page, the user can proceed to a different functional area of the system by clicking one of several link buttons. If the user has administrative privileges (which information is recorded in the user record and assessed by the system when the user logs in), the user may access the administrative part of the system. The administrative area offers site administration functionality, institution-wide reporting functionality, and document approval functionality.

Users who have authority can access the administrative functions, such as the administration and test results reporting. Administrators can control users' categorizations which determine what documents each user is required to review and which require testing. They can also determine which documents are to be hidden from certain users. This information is determined when a user first enters the system and/or when some change occurs, such as a promotion or transfer. Administrators are also responsible for document approval.

Site administration function therefore provides a means to define the organizing structures of the document data and user data, consisting of attributes, categories, sections and linking rules. It also provides a means to control the content of the institution home page.

Certain administrators may be provided with the means to run reports, including graphs, on many aspects of system usage and performance. Reports are custom designed according to the requirements of the institution.

Reporting capability commonly includes frequency of document access by users, as well as individual, group and/or institution-wide test results, summaries, graphs, charts and the like. Further, the status of documents in the review/approval process can be monitored.

The "Priority Policies" function provides a means to display a "Priority Policies" page. Certain documents or groups of documents may be designated as "Priority Policies" if administrators determine that very rapid access to these documents is required. Examples of "Priority Policies" might be the institution's Emergency Preparedness Plan (disaster plan) or Clinical Pathways (formal diagnosis and treatment protocols).

A list of the "Priority Policies" or groups of policies is displayed on the "Priority Policies" page. A means is provided for the user to display a document detail screen for a single document or a policy list for a particular group of priority documents.

Non-administrative users may seek documents meeting particular search criteria (e.g., by department, subject matter, keywords, dates, etc.). Those results can be sorted based on customized parameters (e.g., date or department). A user may limit the search to documents for which the user is responsible or may browse through a table of contents listing documents related to a user-selected category (e.g., a particular department or subject).

The "Search" function provides a means to display the search screen. On this screen, the user can enter criteria such as department, subject, keywords, dates, etc. to specify a subset of documents to search for. The system also provides full-text search capability, permitting searches for any text starting in the HTML versions of documents. The "Search" process is described in FIG. 10.

Figure 11:
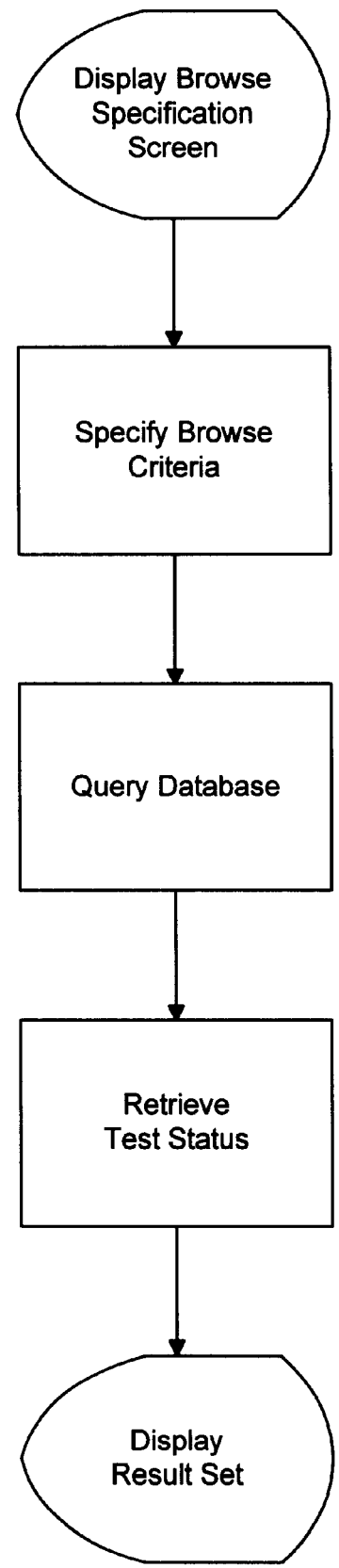
FIG. 11 is a flow chart illustrating the steps involved in browsing for documents.

The "Browse" function provides a means to display the browse screen. On this screen, the user can select a department or other category of documents to search for. The system displays a list of the document titles found in the category selected. The user can then select an individual document to view. The "Browse" process is illustrated in FIG. 11.

Figure 12:
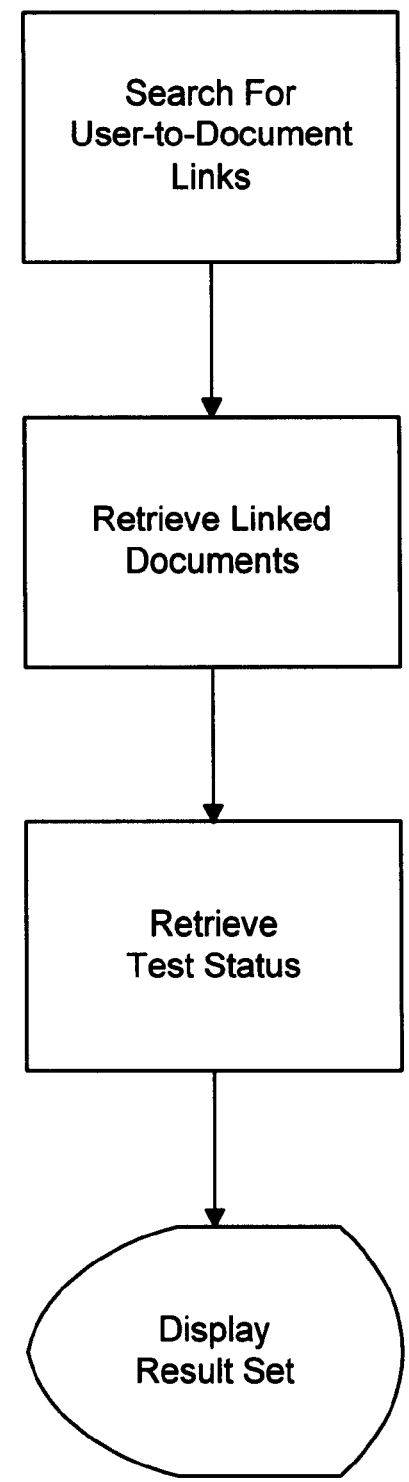
FIG. 12 is a flow chart illustrating the steps involved in creating a list of policies for which a user is responsible.

The "My Policies" function provides a means to display the "My Policies" screen. This screen displays titles of all documents which the user is responsible for knowing and complying with. The process of identifying those documents and displaying the document title is illustrated in FIG. 12.

The system searches the database and retrieves all documents meeting the previously entered "Search", "Browse" or "My Policies" criteria. It displays a list of the document titles, from which the user can select an individual document to view. In addition, the "Policy List" can display one or more columns containing values of selected attributes of the documents listed. The administrators select which attribute values will be displayed in these screens.

The list of documents relating to all policies which the user is responsible for knowing (determined by the attribute management matching rules and/or by manual adjustment) can be displayed. This listing may also indicate which policies the user has previously been tested on and which the user needs to test on. The user's latest review date and prior test scores may also be made available.

Figure 13:
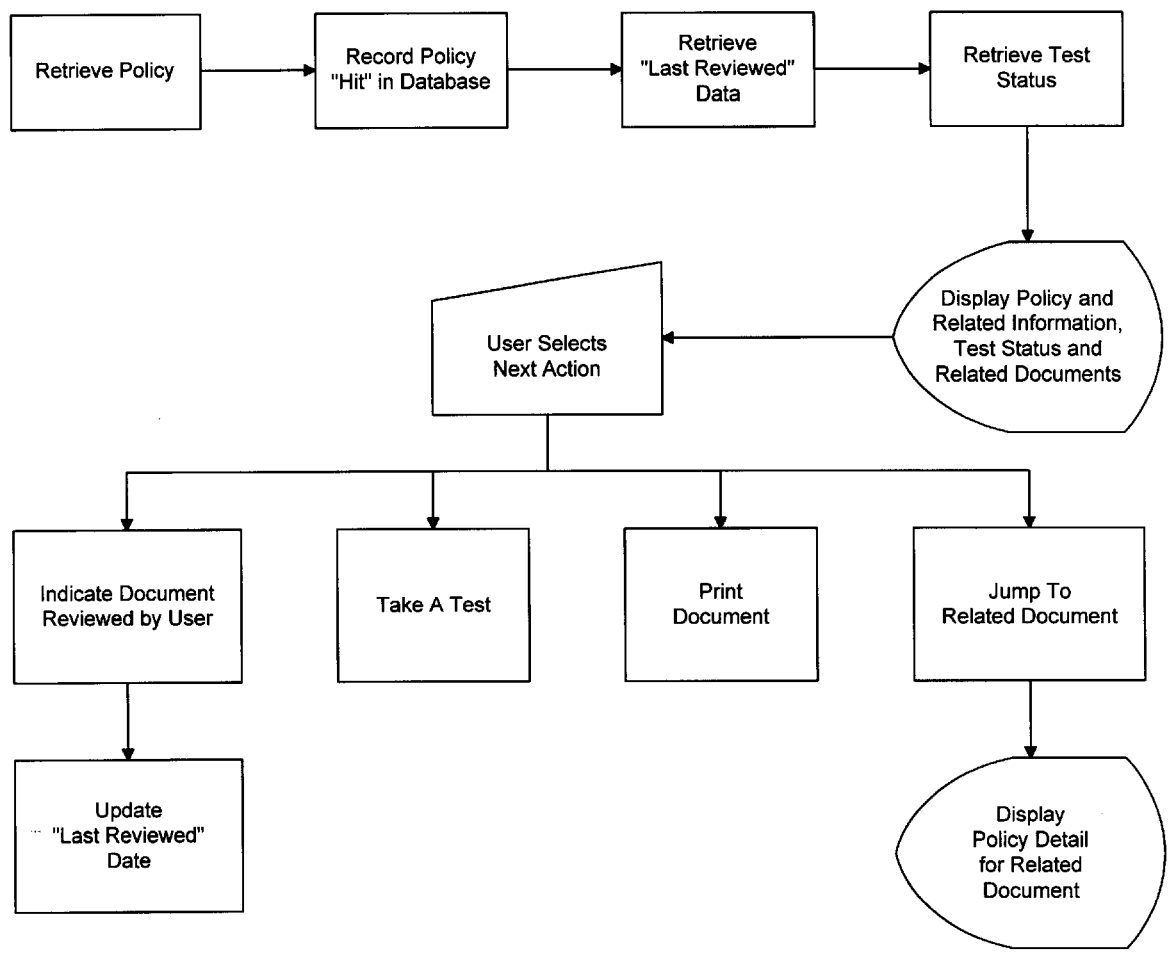
FIG. 13 is a flow chart illustrating the steps involved in retrieving and displaying a policy with related data.

The user selects a document for review. If the user is qualified, he or she may review the document and related information such as the user's test status with regard to the document, related policies and references to other documents. Provision is made for the user to indicate to the system that the document has been reviewed as of that date. This process is illustrated in FIG. 13.

If the user desires to be tested, or if testing is required, the user can request same. When the user indicates readiness to take a test on the document, the system randomly selects a number of questions from the complete list of questions which have been prepared for use in tests on this document. System administrators determine how many questions are selected each time a test is taken on this document. If certain questions in the list have been designated as key questions, they will always be selected, along with other randomly selected non-key questions. In any case, the order in which the questions are displayed is also randomized for each test.

After the user has taken the test, the system scores the test. Test results can be handled in a number of ways, as determined by system administrators. The results are normally displayed for the user, so that the user can assess his own comprehension of the document's content. In addition, the system can save all test scores, the user's latest test score for that document or the user's highest score for that document. The test results, if stored, can be reported to administrators by user, by department, by document, etc. Reports of test scores provide useful information to assist the institution in determining areas in which additional training is needed, as well as documents which may need revision.

In addition, individual users' scores are displayed on the "My Policies" screen to indicate to the user those documents which may require further study.

The stored results are used for tracking each individual user's comprehension of the policies for which he or she is responsible and for department and institution-wide reporting to provide feed-back on compliance generally and specifically to identify policies which may require additional training/reinforcement or revision/clarification.

The system allows the institution to customize the handling of test results on a user-by-user basis. For any set of users, the administrator can choose to save all test results, each user's highest score on each test and/or each user's latest score or to save no results. Also, the user can be permitted the option of deciding whether to save the score.

Figure 10:
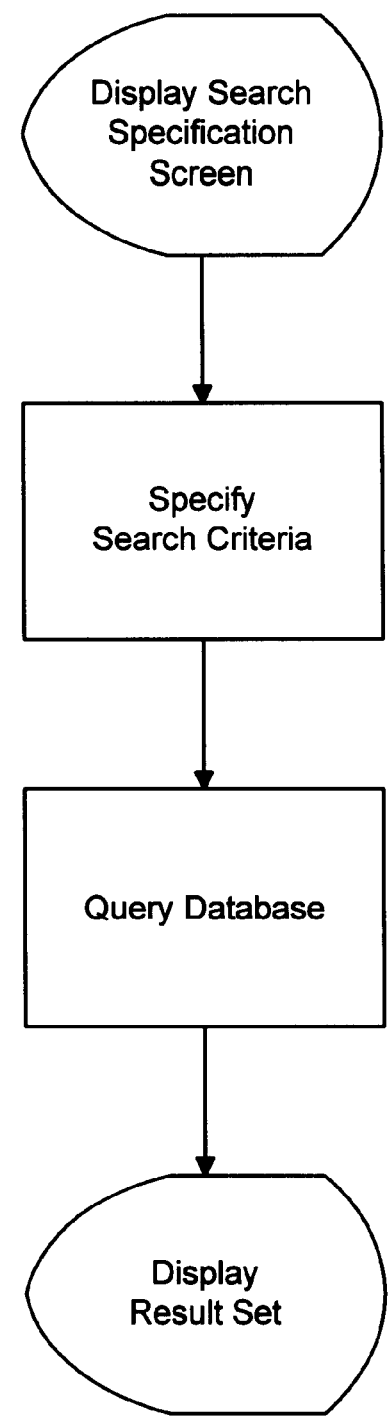
FIG. 10 is a flow chart illustrating the steps involved in a document search.

The "Search" feature is illustrated in FIG. 10. When the user clicks on the "Search" button on the home page, the "Search specification" screen is displayed. On the "Search specification" screen, the user can enter criteria such as keywords, dates, department, or subject, to limit his search. Once the search criteria have been specified, the system searches the database for documents meeting that criteria. The titles of documents found to meet the search criteria are displayed. The user can specify the order in which the documents are displayed, such as by date, by department, etc.

The "Browse" function is illustrated on FIG. 11. When the user clicks on the "Browse" button on the home page, the "Browse specification" screen is displayed. On the "Browse specification" screen, the user can select browse categories. Once a category has been specified, the titles of documents found to meet the browse criteria are displayed. The user can specify the order in which the documents are displayed, such as by date, by department, etc.

The "My Policies" function is illustrated on FIG. 12. This function provides the user with a means to retrieve and display only the policies which he is responsible, making it easier for each user to focus on only the policies which he needs to know. For each document found in the database query, the current user's test results are retrieved. The testing feature provides the user with feedback on his comprehension of the policy and whether further study is indicated. By focusing the user's attention and helping to increase comprehension, the "My Policies" function helps to increase policy compliance.

When the "My Policies" function is accessed by the current user, the system queries the database for User-to-Document Links specifying documents with which the current user is responsible for complying. A list of these links is generated. A list of the document titles specified by each link is retrieved from the database. The user's test status with regard to each of the retrieved documents is retrieved. The list of documents as well as the user's test status with regard to each document is displayed. Thus the display contains all the documents (and only those documents) with which the user is responsible for complying.

The "Policy Detail" function is illustrated in FIG. 13. The "Policy Detail" screen displays the full text of a single policy, with additional information including the last date the user reviewed the policy, the user's test status for that policy, and links to related policies. It provides a means for the user to study the policy, assess his comprehension of it, and seek additional information about the subject. The displays of document titles in the "Search" screen, "Browse" screen and "My Policies" screen provides the user with the means of accessing the full text of any individual document in the list.

The user accesses the display of the full text of an individual document by clicking on the document title. This action causes a "hit" on that document to be recorded in the database, and the full text of the document is retrieved. The date that the current user last reviewed the document is retrieved from the database. The current user's test status with regard to the document is retrieved from the database. The "Policy Detail" page, containing the document text, "Last Reviewed" date and test Status, is displayed. Buttons on the "Policy Detail" screen provide a means for the user to select the next action he wishes to take. Clicking on the "Reviewed" button stores the current date in the database as the last date the current user reviewed the document.

If the user desires to take a test, the user clicks the "Test Button" and the test is formulated. It will include all questions designated as "key" questions. The questions are selected from the complete list and are displayed for the user in random order. A means is provided for the user to indicate his answer to each question. A "Score" button provides a means for the user to submit his answers for scoring when he has finished taking the test. The system calculates the user's score and displays the test questions with the answers, as well as an indication whether the user's answer to each question was correct. The test score is handled in accordance with the instructions of the administrators. The score may be discarded, recorded, or recorded if it is the user's highest score for the current document.

Clicking the "Print" button displays a PDF version of the document suitable for printing. The user can then print the current document. Thus the user can obtain a paper copy of a policy for further off-line study or for making notations about possible revisions before revising the document on-line. The user can also print out a form, which will always be the current version of the form. The cost and effort required to maintain an inventory of forms, as well as the possible of using out-of-date forms, is thereby eliminated.

If the current policy contains links to other documents, the user can jump to any of the linked documents by clicking on the link. If a user clicks on a link to a related document, the "Policy Detail" screen for that document is displayed.

FIG. 14 illustrates how a document is saved in the database. Converted files are stored in subdirectories reflecting the institution's document organization scheme. For example, there may be a subdirectory for each separate policy manual. Each standard format file in a subdirectory is automatically converted to an HTML file, which is stored in the database. A record for each document is also automatically created in a separate database table. Finally, the HTML file of each document is scanned for certain attributes which, if found, are stored in various other database tables.

By a separate process, the same standard format files are converted into PDF format. The PDF versions make it possible for users to print copies of documents that have the same layout and appearance as the original hard copy version of the document. Each PDF file is visually proofed to make sure the converted document is correct and that it will print in the original layout. If the document is incorrect, steps are taken to correct it. Since the PDF version of each document is created from a standard format file, corrections must be made by correcting the standard format file. Once the standard format version is corrected, the PDF file is regenerated and reloaded, and the old PDF version is deleted from the database. Then the above steps are repeated, beginning with proofreading the PDF version.

Depending on the corrections required, it may be necessary to delete and recreate the HTML and other database records relating to the document as well. If the document is correct, the HTML version is scanned visually to be sure the copy is clean. The HTML version is then tagged and edited. Using the Authoring Tool, links to related documents and related sites are tagged. Rules relating to document attributes and user attributes are used to generate links between individual documents and individual users.

A Table of Contents is created manually, based, for example, on the hospital's existing policy manuals. Each document is then associated with the appropriate Table of Contents entry. Each document which has been entered into the system is proofread a final time. The on-line versions of the documents are submitted to the hospital for review and approval.

It will now be appreciated that the present invention relates to a software based interactive system which may be accessed on-line, through a web site or through an intranet home page. Users are identified and view a customized main page. Qualified users may search for and access institution policies for review. Where required, a test is provided. The test results are scored and stored.

Administrative users can set and change user qualification parameters, monitor document status and obtain information as to individual, group and/or institution-wide policy access and test results.

While only a single preferred embodiment of the present invention has been disclosed herein for purposes of illustration, it is obvious that many variations and modifications could be made thereto. It is intended to cover all of these variations and modifications which fall within the scope of the present invention, as defined by the following claims:

We claim:

1. A health care policy document storage and contents comprehension testing system comprising:

means for storing the contents of a plurality of health care policy documents in a database;

means for storing data representing one or more groups of users responsible for comprehending the contents of each of the stored documents;

means for storing data representing one or more groups to which each user is a member;

means for matching the document responsibility data and the user member data to compile a list of documents for which the user is responsible;

means for providing the user with access to review the contents of each stored document on the user's list;

means for indicating whether a test is required for each stored document;

means for preparing and storing a test on the contents of documents for which a test is required;

means for providing the stored test to the user, upon request of the user;

means for scoring the test results; and means for storing the user's test score.

2. The system of claim 1 further comprising means for storing the characteristics of each of the stored documents and for identifying the group or groups of users responsible for comprehending documents with those characteristics.

3. The system of claim 1 further comprising means for storing the attributes of the users which determine to which group or groups the users are a member.

4. The system of claim 1 further comprising means for providing to the user the list of documents for which that user is responsible.

5. The system of claim 1 further comprising means for storing an indication that a user has reviewed a document on the user's list.

6. The system of claim 1 further comprising means for providing the test results to the user.

7. The system of claim 1 further comprising means for identifying qualified administrative users and for reporting the user's test scores to the qualified administrative users.

8. The system of claim 4 further comprising means for tracking when a user accesses a document for review and for reporting same to the qualified administrative users.

9. The system of claim 1 further comprising means for identifying authorized users of the system before providing them with access to review the contents of stored documents.

10. The system of claim 9 further comprising means for making the system accessible to authorized users via the worldwide web.

11. A health care policy document storage and contents comprehension testing method comprising the steps of:

storing the contents of a plurality of health care policy documents in a database;

storing data representing one or more groups of users responsible for comprehending the contents of each of the stored documents;

storing data representing one or more groups of which each user is a member;

matching the document responsibility data and the user member data to compile a list of documents for which the user is responsible;

providing the user with access to review the contents of each stored document on the user's list;

indicating whether a test is required for each stored document;

preparing and storing a test on the contents of documents for which a test is required;

providing the stored test to the user, upon request of the user;

scoring the test results; and storing the user's test score.

12. The method of claim 11 further comprising the step of storing the characteristics of each of the stored documents and identifying the group or groups of users responsible for comprehending documents with those characteristics.

13. The method of claim 11 further comprising the steps of storing the attributes of the users which determine to which group or groups the users are a member.

14. The method of claim 11 further comprising the step of providing to the user the list of documents for which that user is responsible.

15. The method of claim 11 further comprising the step of storing an indication that a user has reviewed a document on the user's list.

16. The method of claim 11 further comprising the step of providing the test results to the user.

17. The method of claim 11 further comprising the step of identifying qualified administrative users and reporting the test results to the qualified administrative users.

18. The method of claim 17 further comprising the step of tracking when a user accesses a document for review and reporting same to the qualified administrative user.

19. The method of claim 11 further comprising the step of identifying authorized users of the system before providing them with access to review the contents of stored documents.

20. The method of claim 19 further comprising the step of making the system accessible to authorized users via the worldwide web.

* * * * *